US011352653B2

(12) United States Patent
Tao et al.

(10) Patent No.: US 11,352,653 B2
(45) Date of Patent: Jun. 7, 2022

(54) ENZYMATIC METHOD FOR PREPARING REBAUDIOSIDE N

(71) Applicant: PepsiCo, Inc., Purchase, NY (US)

(72) Inventors: Alex Tao, Jiangsu (CN); Guoqing Li, Jiangsu (CN); Wenxia Wang, Jiangsu (CN); Leilei Zheng, Jiangsu (CN); Chunlei Zhu, Jiangsu (CN); Xiaoliang Liang, Jiangsu (CN); Kuikiu Chan, Jiangsu (CN)

(73) Assignee: PEPSICO, INC., Purchase, NY (US)

( * ) Notice: Subject to any disclaimer, the term of this patent is extended or adjusted under 35 U.S.C. 154(b) by 344 days.

(21) Appl. No.: 16/343,335

(22) PCT Filed: Oct. 21, 2016

(86) PCT No.: PCT/CN2016/102948
§ 371 (c)(1),
(2) Date: Jul. 12, 2019

(87) PCT Pub. No.: WO2018/072213
PCT Pub. Date: Apr. 26, 2018

(65) Prior Publication Data
US 2021/0214761 A1 Jul. 15, 2021

(51) Int. Cl.
C12P 19/56 (2006.01)
C12N 9/10 (2006.01)
C12P 7/40 (2006.01)

(52) U.S. Cl.
CPC ............ C12P 19/56 (2013.01); C12N 9/1048 (2013.01); C12N 9/10 (2013.01); C12P 7/40 (2013.01); C12Y 204/01017 (2013.01)

(58) Field of Classification Search
CPC ...... C12P 19/56; C12P 7/40; A23V 2250/258; C12N 9/1051; C12N 9/1048; A23L 2/60; A23L 27/30; C12Y 204/01017; C12Y 204/01; C12Y 204/99
USPC ................. 435/78, 193, 200, 252.3, 252.33; 426/548, 658
See application file for complete search history.

(56) References Cited

U.S. PATENT DOCUMENTS

| 9,243,273 | B2 | 1/2016 | Markosyan et al. |
| 9,752,174 | B2 | 9/2017 | Markosyan |
| 10,301,662 | B2 | 5/2019 | Tao et al. |
| 2010/0099857 | A1 | 4/2010 | Evans |
| 2011/0218161 | A1 | 9/2011 | Han et al. |
| 2013/0171328 | A1 | 7/2013 | Kishore et al. |
| 2014/0271996 | A1 | 9/2014 | Prakash et al. |
| 2014/0296499 | A1 | 10/2014 | Chen et al. |
| 2014/0357588 | A1 | 12/2014 | Markosyan |
| 2015/0315623 | A1 | 11/2015 | Mao et al. |
| 2016/0186225 | A1 | 6/2016 | Mikkelsen |
| 2016/0298159 | A1 | 10/2016 | Tao et al. |
| 2017/0211113 | A1 | 7/2017 | Tao et al. |
| 2018/0320211 | A1 | 11/2018 | Du et al. |

FOREIGN PATENT DOCUMENTS

| CA | 2 913 252 A1 | 12/2014 |
| CN | 103031283 A | 4/2013 |
| CN | 103088041 A | 5/2013 |
| CN | 103179850 A | 6/2013 |
| CN | 103397064 A | 11/2013 |
| CN | 106471128 A | 1/2014 |
| CN | 103757074 A | 4/2014 |
| CN | 105200098 A | 12/2015 |
| JP | 2010-538621 | 12/2010 |
| JP | 2012-504552 A | 2/2012 |
| RU | 2 596 190 C9 | 10/2016 |
| WO | WO 2010/038911 A1 | 4/2010 |
| WO | WO 2011/046423 A1 | 4/2011 |
| WO | WO 2011/153378 A1 | 12/2011 |
| WO | WO 2012/103074 A2 | 8/2012 |
| WO | WO 2013/022989 A2 | 2/2013 |
| WO | WO 2013/096420 A1 | 6/2013 |
| WO | WO 2013/110673 A1 | 8/2013 |
| WO | WO 2013/176738 A1 | 11/2013 |
| WO | WO 2014/086890 A1 | 6/2014 |
| WO | WO 2014/122227 A2 | 8/2014 |
| WO | WO 2015/021690 A1 | 2/2015 |
| WO | WO-2015065650 A2 | 5/2015 |
| WO | WO 2015/094117 A1 | 6/2015 |
| WO | WO 2015/113231 A1 | 8/2015 |
| WO | WO2016/028899 A1 | 2/2016 |
| WO | WO 2016/054534 A1 | 4/2016 |
| WO | WO 2016/120486 A1 | 8/2016 |
| WO | WO 2016/196345 A1 | 12/2016 |

(Continued)

OTHER PUBLICATIONS

Kisselev L., Structure, 2002, vol. 10: 8-9.*
Witkowski et al., Biochemistry 38:11643-11650, 1999.*
Whisstock et al., Quarterly Reviews of Biophysics 2003, vol. 36 (3): 307-340.*
Devos et al., Proteins: Structure, Function and Genetics, 2000, vol. 41: 98-107.*
Genbank, "UDP-glycosyltransferase 76G1 [Stevia rebaudiana]," Accession No. AAR06912.1, accessed at http://www.ncbi.nlm.nih.gov/protein/AAR06912, accessed on May 26, 2016, 2 pages.

(Continued)

Primary Examiner — Robert B Mondesi
Assistant Examiner — Mohammad Y Meah
(74) Attorney, Agent, or Firm — Sterne, Kessler, Goldstein & Fox P.L.L.C.

(57) ABSTRACT

Provided is a method for preparing rebaudioside N using an enzymatic method, comprising using rebaudioside A or rebaudioside J as a substrate, and making the substrate, in the presence of a glycosyl donor, react under the catalysis of a UDP-glycosyl-transferase and/or a UDP-glycosyltransferase-containing recombinant cell to generate rebaudioside N.

11 Claims, No Drawings
Specification includes a Sequence Listing.

(56) References Cited

FOREIGN PATENT DOCUMENTS

WO    WO 2017/031424 A1    2/2017

OTHER PUBLICATIONS

Genbank, "Os03g0702000 [*Oryza saliva japonica* Group]," Accession No. NP_00 1051007.2, accessed at http://www.ncbi.nlm.nih.gov/protein/NP_001051007.2?report=genpept, accessed on May 26, 2016, 4 pages.
Masada, S., et al., "An efficient chemoenzymatic production of small molecule glucosides with in situ UDP-glucose recycling," *FEBS Letters* 581(13):2562-2566, Elsevier B.V., Netherlands (2007).
Ohta, M., et al., "Characterization of Novel Steviol Glycosides from Leaves of *Stevia rebaudiana* Morita," *J. Appl. Glycosci.* 57(3): 199-209, The Japanese Society of Applied Glycoscience, Japan (2010).
Wang, Q.J., et al., "*Saccharomyces cerevisiae* surface expression of sucrose synthase," China resources biotechnology and enzyme engineering symposium proceedings (2005).
Wölwer-Rieck, U., "The leaves of Stevia rebaudiana (Bertoni), their constituents and the analyses thereof: a review," *J Agric Food Chem.* 60(4) :886-895, American Chemical Society, United States (2012).
Co-pending U.S. Appl. No. 16/343,339, inventors Tao, A., et al., filed Oct. 21, 2016 (Not Published).
Pearson, W.R., "An Introduction to Sequence Similarity ("Homology") Searching," *Curr Protoc Bioinformatic*, Author Manuscript, Jun. 3, Wiley, USA (2013).
Whisstock et al., "Prediction of protein function from protein sequence and stucture," Quarterly Reviews of Biophysics 36(3): 307-340 (2003).
Witkowski et al., "Conversion of a beta-ketoacyl synthase to a malonyl decarboxylase by replacement of the active-site cysteine with glutamine," Biochemistry 38(36): 11643-11650 (1999).
Chen, R.R., "Permeability issues in whole-cell bioprocesses and cellular membrane engineering," Appl Microbial Biotechnol 74:730-738 (2007).
UniProtKB-F2DT21 (F2DT21_HORVD), May 31, 2011, accessed at http://www.uniprot.org/uniprot/F2DT21, 4 pages.
Co-pending U.S. Appl. No. 15/932,218, inventors Anderson, A., et al., filed Aug. 19, 2016 (Not Published).
Co-pending U.S. Appl. No. 16/380,678, inventors Tao, J., et al., filed Apr. 10, 2019 (Not Published).
Son, M.H., et al., "Production of Flavonoid O-Glucoside Using Sucrose Synthase and Flavonoid O-Glucosyltransferase Fusion Protein," J. Microbiol. Biotechnol. 19(7):709-12, Springer Nature, Switzerland (2009).
Mohamed, A. A. et al., "UDP-dependent glycosyltransferases involved in the biosynthesis of steviol glycosides," J Plant Physiol. 168(10): 1136-41, Elsevier, Netherlands (2011).
Branden, C. et al., "Prediction, Engineering, and Design of Protein Structures," Introduction to Protein Structure, Garland Publishing Inc., New York, p. 247 (1991).
Studer, R. A. et al., "Residue mutations and their impact on protein structure and function: detecting beneficial and pathogenic changes," Biochem. J. 449:581-594, Biochemical Society, England (2013).
Co-pending U.S. Appl. No. 16/343,340, inventors Tao, A., et al., filed Oct. 21, 2016 (Not Published).
Xu, L. et al., "Progress and strategies on bioethanol production from liganocellulose by consolidated bioprocessing (CBP) using *Saccharyomyces cerevisiae*," *Chinese Journal of Biotechnology* 26(7): 870-879 (2010).
English Translation of the Written Opinion for International Application No. PCT/CN2016/102948, State Intellectual Property Office of the P.R. China, China, dated Jul. 18, 2017, 3 pages.
English Translation of the International Preliminary Report on Patentability for International Application No. PCT/CN2016/102948, State Intellectual Property Office of the P.R. China, China, dated Apr. 23, 2019, 4 pages.
English Translation of the Written Opinion for International Application No. PCT/CN2016/102910, State Intellectual Property Office of the P.R. China, China, dated Jul. 14, 2017, 3 pages.
English Translation of the International Preliminary Report on Patentability for International Application No. PCT/CN2016/102910, State Intellectual Property Office of the P.R. China, China, dated Apr. 23, 2019, 4 pages.
English Translation of the Written Opinion for International Application No. PCT/CN2016/102942, State Intellectual Property Office of the P.R. China, China, dated Jul. 12, 2017, 4 pages.
English Translation of the International Preliminary Report on Patentability for International Application No. PCT/CN2016/102942, State Intellectual Property Office of the P.R. China, China, dated Apr. 23, 2019, 5 pages.
Supplementary European Search Report for EP Application No. EP 16 91 9469, Berlin, Germany, dated Jun. 24, 2020, 2 pages.
Supplementary European Search Report for EP Application No. EP 16 91 9379, Berlin, Germany, dated Jun. 18, 2020, 3 pages.

\* cited by examiner

SEQUENCE LISTING

```
<160> NUMBER OF SEQ ID NOS: 4

<210> SEQ ID NO 1
<211> LENGTH: 1377
<212> TYPE: DNA
<213> ORGANISM: Artificial Sequence
<220> FEATURE:
<223> OTHER INFORMATION: Stevia
```

<400> SEQUENCE: 1

```
atggaaaaca aaaccgaaac cacggtacgc cgtcgtcgtc gtatcatcct cttcccggtt      60
ccgtttcagg gtcacatcaa cccgatcctt cagttggcaa acgtactgta ctctaaaggt     120
tttagcatca ccattttca cactaacttt aacaaaccga aacctctaa ctatccgcac       180
ttcactttcc gcttcatcct ggacaacgac ccgcaagatg agcgcattag caacctgccg     240
acccatggcc cgctggcagg catgcgcatc cctatcatca tgaacacgg cgctgacgaa      300
ctgcgtcgtg agctggaact cctgatgctg gcttctgaag aagacgagga agtgtcttgc     360
ctgattacag acgctctctg gtactttgct cagagcgtgg cggactctct gaacctgcgc     420
cgtctggttc ttatgacttc ttccttgttt aatttccatg cgcatgtctc tctgccgcag     480
ttcgacgagc tgggctacct ggacccggat gacaaaactc gcctggagga acaggcatct     540
ggcttcccga tgctgaaagt aaaagatatc aaagcgcat actccaattg cagatcctg      600
aaagagattc tgggcaaaat gatcaagcag actaaagcat ccagcggcgt tatctggaac     660
tcctttaaag agctggagga agcgaactg gaaaccgtga tccgtgaaat cccggcaccg     720
tcgttcctga ttcctctgcc taaacatctg accgcctcct cttcttctct gctggatcac     780
gatcgcaccg tttccagtg gctggatcag caaccgccga ttctgtgct gtatgttct       840
tccggctcga cgagtgaggt tgacgaaaaa gacttcctgg aaatcgcacg cggcctggtt     900
gactctaaac agagctttct gtgggttgta cgtccgggtt cgtgaaggg cagcacctgg     960
gttgaaccgc tgccggacgg cttttttgggc gaacgcggcc gtatcgtaaa atgggtaccg    1020
cagcaggagg tactggcaca cggcgcaatt ggggcgttct ggactcactc cggctggaac    1080
tccactctgg aatccgtatg cgaaggcgtt cctatgattt cagcgactt cggcctggat     1140
cagccgctga acgcacgcta tgtcagac gttctgaaag tcggtgtgta tctggagaac      1200
gggtgggagc gtggcgaaat tgccaacgcg atccgtcgtg ttatggtgga tgaagaaggc     1260
gaatacatcc gtcagaacgc tcgtgtcctt aaacagaaag ctgacgtgag cctgatgaaa    1320
ggtggctcta gctacgaatc gctggagtcc ctggtttctt acatctcgtc gctgtaa       1377
```

<210> SEQ ID NO 2
<211> LENGTH: 458
<212> TYPE: PRT
<213> ORGANISM: Artificial Sequence
<220> FEATURE:
<223> OTHER INFORMATION: Stevia

<400> SEQUENCE: 2

```
Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
            20                  25                  30

Ala Asn Val Leu Tyr Ser Lys Gly Phe Ser Ile Thr Ile Phe His Thr
        35                  40                  45

Asn Phe Asn Lys Pro Lys Thr Ser Asn Tyr Pro His Phe Thr Phe Arg
    50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110
```

Glu Glu Asp Glu Glu Val Ser Cys Leu Ile Thr Asp Ala Leu Trp Tyr
            115                 120                 125

Phe Ala Gln Ser Val Ala Asp Ser Leu Asn Leu Arg Arg Leu Val Leu
130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Lys Thr Arg Leu Glu
            165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
            245                 250                 255

Leu Leu Asp His Asp Arg Thr Val Phe Gln Trp Leu Asp Gln Gln Pro
        260                 265                 270

Pro Ser Ser Val Leu Tyr Val Ser Phe Gly Ser Thr Ser Glu Val Asp
    275                 280                 285

Glu Lys Asp Phe Leu Glu Ile Ala Arg Gly Leu Val Asp Ser Lys Gln
    290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
            325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
        355                 360                 365

Gly Val Pro Met Ile Phe Ser Asp Phe Gly Leu Asp Gln Pro Leu Asn
    370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
            405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
        435                 440                 445

Glu Ser Leu Val Ser Tyr Ile Ser Ser Leu
    450                 455

<210> SEQ ID NO 3
<211> LENGTH: 1389
<212> TYPE: DNA
<213> ORGANISM: Artificial Sequence
<220> FEATURE:
<223> OTHER INFORMATION: rice

<400> SEQUENCE: 3
atggacagcg gttactcttc tagctatgct gcggcagccg gtatgcacgt agttatttgt    60

```
ccgtggctcg ctttcggtca cctcctgccg tgcctggacc tggcgcagcg cctggcatct      120
cgtggtcacc gtgtcagttt cgttagcacg ccgcgtaaca tctcacgtct gccgccggtc      180
cgtccggctc tggccccgct ggttgcgttc gttgcgctac ctctgccgcg cgttgaaggc      240
ttaccggatg gcgcagagtc taccaacgac gtgccgcacg atcgcccgga tatggttgaa      300
ctccaccgcc gtgcatttga cggtctggca gctccgttct ccgaatttct gggtaccgcg      360
tgtgccgact gggtcatcgt agacgtattc caccactggg cagctgcagc ggctttagaa      420
cacaaagtac cgtgcgcaat gatgctgctg ggctctgctc acatgatcgc gtctattgcc      480
gaccgtcgtc tggaacgtgc agagaccgaa tctccagcgg cagccggtca gggccgtcct      540
gcagctgctc cgaccttcga agttgctcgt atgaagctca tccgcactaa aggttcttcc      600
ggtatgtcac tggcagagcg tttctcgctg acgctctccc gtagcagcct ggttgtgggg      660
cgctcctgcg tggaattcga accggaaact gtgccgctac tgtctaccct gcgtggcaag      720
ccgatcactt ttctgggtct catgccgcca ctgcacgaag gtcgccgcga agacggtgaa      780
gatgctacgg ttcgttggtt ggacgcccag ccggctaaaa gcgtcgtgta cgtagctctg      840
ggcagtgaag ttccattggg tgtcgagaaa gtgcatgaac tggctttggg tctggagctg      900
gctggcaccc gtttcctctg gcactgcgt aagccgactg gtgtgtctga tgctgacctt      960
ctgccggctg gtttcgaaga acgtacccgt ggtcgcggcg tagtggcaac ccgctgggta     1020
ccgcagatgt ccatcctggc acacgctgct gttggcgcgt tcttaccca ctgcgggtgg      1080 aactctacaa tcgaaggcct gatgttcggc catcctctga ttatgctgcc aatcttcggt     1140
gatcagggtc cgaacgctcg tctgatcgaa gccaaaaacg ccggcttaca agtcgcacgc     1200
aacgacggcg atggttcttt cgatcgtgaa ggtgttgcgg cagctatccg tgcagtggct     1260
gtagaagaag agtcgagcaa agtgttccag gcaaaagcca aaaagctgca ggaaatcgtt     1320
gcggacatgg cgtgccacga acgttacatc gatggcttta ccagcagct gcgctcctac      1380 aaagattaa                                                             1389
```

<210> SEQ ID NO 4
<211> LENGTH: 462
<212> TYPE: PRT
<213> ORGANISM: Artificial Sequence
<220> FEATURE:
<223> OTHER INFORMATION: rice

<400> SEQUENCE: 4

```
Met Asp Ser Gly Tyr Ser Ser Ser Tyr Ala Ala Ala Gly Met His
1               5                   10                  15

Val Val Ile Cys Pro Trp Leu Ala Phe Gly His Leu Leu Pro Cys Leu
                20                  25                  30

Asp Leu Ala Gln Arg Leu Ala Ser Arg Gly His Arg Val Ser Phe Val
            35                  40                  45

Ser Thr Pro Arg Asn Ile Ser Arg Leu Pro Pro Val Arg Pro Ala Leu
        50                  55                  60

Ala Pro Leu Val Ala Phe Val Ala Leu Pro Leu Pro Arg Val Glu Gly
65                  70                  75                  80

Leu Pro Asp Gly Ala Glu Ser Thr Asn Asp Val Pro His Asp Arg Pro
                85                  90                  95

Asp Met Val Glu Leu His Arg Arg Ala Phe Asp Gly Leu Ala Ala Pro
            100                 105                 110

Phe Ser Glu Phe Leu Gly Thr Ala Cys Ala Asp Trp Val Ile Val Asp
        115                 120                 125
```

-continued

```
Val Phe His His Trp Ala Ala Ala Ala Ala Leu Glu His Lys Val Pro
    130                 135                 140
Cys Ala Met Met Leu Leu Gly Ser Ala His Met Ile Ala Ser Ile Ala
145                 150                 155                 160
Asp Arg Arg Leu Glu Arg Ala Glu Thr Glu Ser Pro Ala Ala Ala Gly
                165                 170                 175
Gln Gly Arg Pro Ala Ala Ala Pro Thr Phe Glu Val Ala Arg Met Lys
                180                 185                 190
Leu Ile Arg Thr Lys Gly Ser Ser Gly Met Ser Leu Ala Glu Arg Phe
            195                 200                 205
Ser Leu Thr Leu Ser Arg Ser Ser Leu Val Val Gly Arg Ser Cys Val
    210                 215                 220
Glu Phe Glu Pro Glu Thr Val Pro Leu Leu Ser Thr Leu Arg Gly Lys
225                 230                 235                 240
Pro Ile Thr Phe Leu Gly Leu Met Pro Pro Leu His Glu Gly Arg Arg
                245                 250                 255
Glu Asp Gly Glu Asp Ala Thr Val Arg Trp Leu Asp Ala Gln Pro Ala
                260                 265                 270
Lys Ser Val Val Tyr Val Ala Leu Gly Ser Glu Val Pro Leu Gly Val
            275                 280                 285
Glu Lys Val His Glu Leu Ala Leu Gly Leu Glu Leu Ala Gly Thr Arg
    290                 295                 300
Phe Leu Trp Ala Leu Arg Lys Pro Thr Gly Val Ser Asp Ala Asp Leu
305                 310                 315                 320
Leu Pro Ala Gly Phe Glu Glu Arg Thr Arg Gly Arg Gly Val Val Ala
                325                 330                 335
Thr Arg Trp Val Pro Gln Met Ser Ile Leu Ala His Ala Ala Val Gly
                340                 345                 350
Ala Phe Leu Thr His Cys Gly Trp Asn Ser Thr Ile Glu Gly Leu Met
            355                 360                 365
Phe Gly His Pro Leu Ile Met Leu Pro Ile Phe Gly Asp Gln Gly Pro
    370                 375                 380
Asn Ala Arg Leu Ile Glu Ala Lys Asn Ala Gly Leu Gln Val Ala Arg
385                 390                 395                 400
Asn Asp Gly Asp Gly Ser Phe Asp Arg Glu Gly Val Ala Ala Ala Ile
                405                 410                 415
Arg Ala Val Ala Val Glu Glu Glu Ser Ser Lys Val Phe Gln Ala Lys
                420                 425                 430
Ala Lys Lys Leu Gln Glu Ile Val Ala Asp Met Ala Cys His Glu Arg
            435                 440                 445
Tyr Ile Asp Gly Phe Ile Gln Gln Leu Arg Ser Tyr Lys Asp
    450                 455                 460
```

ENZYMATIC METHOD FOR PREPARING REBAUDIOSIDE N

REFERENCE TO SEQUENCE LISTING SUBMITTED ELECTRONICALLY

The content of the electronically submitted sequence listing, (file name: 3711_9300000_SequenceListing.txt; size: 12,144 bytes; and date of creation: Apr. 15, 2019), filed herewith, is incorporated herein by reference in its entirety.

FIELD OF INVENTION

The present invention relates to a method for preparing rebaudioside N using an enzymatic method, and in particular, relates to biological preparation method of rebaudioside N.

BACKGROUND

Sweeteners are a kind of food additives widely used in the production of foods such as beverages and confectionery. The sweeteners may be added either during the production of foods or used, through appropriate dilution, as substitutes for sucrose in household baking. The sweeteners include natural sweeteners and artificial sweeteners, the former including sucrose, high fructose corn syrup, honey, and the like, the latter including aspartame, saccharin, and the like. Stevioside is a type of natural sweetening agent extracted from *Stevia rebaudiana* plant, and now has been widely used in food and beverages. Extracts of *Stevia rebaudiana* contain a plurality of steviosides comprising rebaudioside, and naturally extracted steviosides have larger difference in composition batch by batch, which need to be subsequently purified.

The ratio of rebaudioside N in *Stevia rebaudiana* leaves is less than 1.5%. It is extremely difficult to obtain high-purity rebaudioside N by traditional extraction methods, which limits the in-depth study of rebaudioside N and hinders its commercial application.

SUMMARY

The technical problem to be solved by the present invention is to overcome the defects in the prior art, and provide a method for preparing rebaudioside N using an enzymatic method. According to the method, high-purity rebaudioside N products may be prepared with a low cost in a short production cycle.

The following technical solution is employed by the present invention to solve the technical problem described above.

A method for preparing rebaudioside N using an enzymatic method is provided. The method comprises: using rebaudioside A as a substrate, in the presence of a glycosyl donor, reacting under catalysis of a UDP-glycosyltransferase-containing recombinant cell and/or a prepared UDP-glycosyltransferase to generate the rebaudioside N.

A method for preparing rebaudioside N using an enzymatic method is further provided. The method comprises: using rebaudioside J as a substrate, in the presence of a glycosyl donor, reacting under catalysis of a UDP-glycosyltransferase-containing recombinant cell and/or, a prepared UDP-glycosyltransferase to generate the rebaudioside N.

Preferably, the glycosyl donor comprises one or two of a glucose-based donor and a rhamnosyl donor; wherein the glucose-based donor is UDP-glucose or a UDP-glucose regeneration system (2007, *FEBS Letters*, 581, 2562-2566) consisting of sucrose, sucrose synthase and UDP, and the rhamnosyl donor is UDP-rhamnose. The glucose-based donor is preferably the UDP-glucose regeneration system consisting of sucrose, sucrose synthase and UDP. The price of the UDP glucose is high. Therefore, use of the UDP-glucose regeneration system may greatly lower the cost.

Preferably, the UDP-glycosyltransferase (that is, uridine diphosphate glucanotransferase, which is referred to as UGT for short, and is known in the art) comprises one or two of UGT-A from *Stevia rebaudiana* and UGT-B from *Oryza sativa*.

Preferably, the UDP-glycosyltransferase comprises UGT-A from *Stevia rebaudiana* and UGT-B from *Oryza sativa*; the UDP-glycosyltransferase is added into the reaction system in two steps; wherein the UGT-B is added in the first step and the UGT-A is added in the second step. An amino acid sequence of the UGT-A has at least 60% identity to sequence 2 listed in a sequence listing; and/or an amino acid sequence of the UGT-B has at least 60% identity to sequence 4 listed in the sequence listing.

More preferably, the amino acid sequence of the UGT-A has at least 70% identity to sequence 2 listed in the sequence listing; and/or the amino acid sequence of the UGT-B has at least 70% identity to sequence 4 listed in the sequence listing.

Further, the amino acid sequence of the UGT-A has at least 80% identity to sequence 2 listed in the sequence listing; and/or the amino acid sequence of the UGT-B has at least 80% identity to sequence 4 listed in the sequence listing.

Still further, the amino acid sequence of the UGT-A has at least 90% identity to sequence 2 listed in the sequence listing; and/or the amino acid sequence of the UGT-B has at least 90% identity to sequence 4 listed in the sequence listing.

In some specific embodiments, the amino acid sequence of the UGT-A is absolutely identical to sequence 2 listed in the sequence listing; and/or the amino acid sequence of the UGT-B is absolutely identical to sequence 4 listed in the sequence listing.

Preferably, the UDP-glycosyltransferase is UGT-A from *Stevia rebaudiana*; wherein an amino acid sequence of the UGT-A has at least 60% identity to sequence 2 listed in a sequence listing.

More preferably, the amino acid sequence of the UGT-A has at least 70% identity to sequence 2 listed in the sequence listing.

Further, the amino acid sequence of the UGT-A has at least 80% identity to sequence 2 listed in the sequence listing.

Still further, the amino acid sequence of the UGT-A has at least 90% identity to sequence 2 listed in the sequence listing. In some specific embodiments, the amino acid sequence of the UGT-A is absolutely identical to sequence 2 listed in the sequence listing.

According to the present invention, the reaction is carried out in an aqueous phase system at a temperature of 4 to 50° C. and a pH value of 5.0 to 9.0. Preferably, the reaction is carried out in an aqueous phase system at a temperature of 35 to 45° C. and a pH value of 7.5 to 8.5.

More preferably, the reaction is carried out in a phosphate buffer solution.

More preferably, the reaction system comprises a UDP-glycosyltransferase recombinant cell and a cell permeabilizing agent. Further, cell permeabilizing agent is toluene;

wherein the toluene has a volume specific concentration of 1 to 3% in the reaction system.

More preferably, all the starting materials used for the reaction are added into a reaction vessel, mixed uniformly and placed at a set temperature, and stirred for sufficient reaction. Upon completion of the reaction, a rebaudioside N product satisfying the using requirement may be obtained by purification. A specific purification method is post-treatment including resin separation. According to this purification method, a rebaudioside N product having a purity reaching 95% may be obtained.

Preferably, the recombinant cell is a microbial cell. More preferably, the microorganism is *Escherichia coli, Saccharomyces cerevisiae* or *Pichia pastoris*.

According to a specific aspect of the present invention, a reaction substrate in the first step is rebaudioside A, and the UDP-glycosyltransferase is UGT-B from *Oryza sativa*, wherein an amino acid sequence of the UGT-B from *Oryza sativa* has at least 80% identity to sequence 4; and a reaction substrate in the second step is a reaction solution containing a reaction product rebaudioside J from the first step, and the UDP-glycosyltransferase is UGT-A from *Stevia rebaudiana*, wherein an amino acid sequence of the UGT-A from *Stevia rebaudiana* has at least 80% identity to sequence 2.

According to another specific aspect of the present invention, a reaction substrate is rebaudioside J, the UDP-glycosyltransferase is UGT-A from *Stevia rebaudiana*, wherein an amino acid sequence of the UGT-A from *Stevia rebaudiana* has at least 80% identity to sequence 2.

Compared with the prior art, the present invention has the following advantages by performing the foregoing technical solution:

The method for preparing rebaudioside N using an enzymatic method according to the present invention has a very significant application value. Since the microorganisms grow far more faster than the plants, by this method, the production cost may be greatly lowered, the production cycle may be shortened and the competitiveness of products may be greatly improved. In addition, the plants have a low content of steviosides, but contain a large number of steviosides with different structures. Therefore, it is difficult to extract purer products. As compared with the conventional technique of extracting rebaudioside N from the leaves of *Stevia rebaudiana*, the enzymatic synthesis method according to the present invention may achieve products having a higher purity, and inevitably promotes studies and application of novel stevioside-type rebaudioside N.

DETAILED DESCRIPTION OF THE INVENTION

Formula I and formula II are structural formulae of rebaudioside J and rebaudioside N.

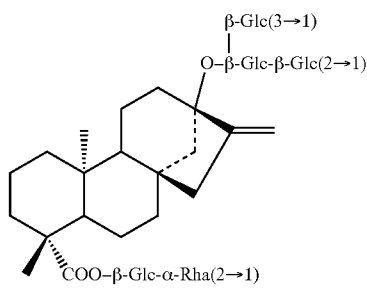

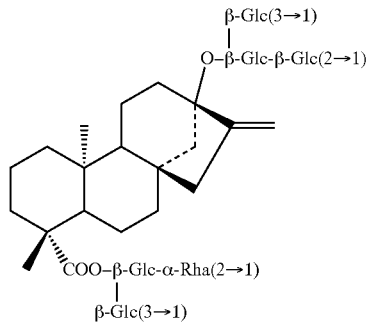

The present invention mainly provides two routes for synthesizing the rebaudioside N.

Route One:

Route Two:

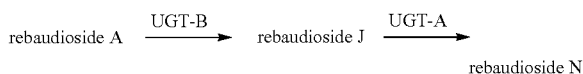

The UGT-A or UGT-B used in the present invention may be present in an enzyme lyophilized powder form or present in a recombinant cell.

The method for obtaining UGT-A or UGT-B is as follows:

Expression strains of recombinant *Escherichia coli* (or other microorganisms) are obtained by the molecular cloning technique and genetic engineering technique, and then the recombinant *Escherichia coli* is fermented to obtain recombinant cells containing the UGT-A or the UGT-B; or lyophilized powder of the UGT-A or the UGT-B is prepared from the recombinant cells.

The molecular cloning technique and the genetic engineering technique according to the present invention are both known. For details about the molecular cloning technique, reference may be made to Molecular Cloning: A laboratory Manual, third version (by Joseph Sambrook, 2005).

The expression steps of the recombinant strain herein constructed by employing genetic engineering technique are as follows:

(1) Desired gene fragments are genetically synthesized (based on sequence 1 and sequence 2 or sequence 3 and sequence 4 listed in the sequence listing), and ligated into a vector pUC57, wherein NdeI and BamHI enzyme digestion sites are loaded at two terminals thereof.

(2) By double enzyme digestion and linking, the gene fragments are inserted into the corresponding enzyme digestion sites of a expression vector pTE30a, such that the genes are placed under control of a T7 promoter.

(3) The recombinant plasmids are transformed and placed into the *Escherichia coli* BL21 (DE3), and a target protein expression is induced by IPTG, such that the recombinant *Escherichia coli* expression strains containing the UGT-A or the UGT-B are obtained.

The recombinant cells containing the UGT-A or the UGT-B, and the lyophilized powder of the UGT-A or the UGT-B are prepared by using the recombinant *Escherichia coli* expression strains containing the UGT-A or the UGT-B by the following steps:

The recombinant *Escherichia coli* expression strains containing the UGT-A or the UGT-B are inoculated at a proportion of 1% into a 4 ml liquid LB medium, and the medium is shaken (at a speed of 200 rpm) at 37° C. overnight; the overnight culture is transferred at an inoculation amount of 1% into a 50 ml liquid LB medium, and is inoculated by shaking (at a speed of 200 rpm) at 37° C. until the OD600 value reaches the range of 0.6 to 0.8; and then the IPTG having a concentration of 0.4 mM is added and overnight inoculation is carried out by shaking at 20° C. Upon completion of inducement, cells are centrifuged (8000 rpm and 10 min) and collected, the cells are resuspended by using a 5 ml 2 mmol/L phosphate buffer (having a pH value of 7.0) to obtain the recombinant cells. The obtained recombinant cells are further treated in ice bath and are ultrasonically crushed. A crushing liquid is centrifuged (8000 rpm and 10 min). Afterwards, a supernatant is collected and lyophilized for 24 h to obtain the lyophilized powder.

The present invention is described in detail hereinafter with reference to specific examples.

Example 1: Preparation of Recombinant *Escherichia coli* Cells Containing the UGT-A In accordance with sequence 1 and sequence 2 listed in the sequence listing, the UGT-A gene fragments are genetically synthesized, NdeI and BamHI enzyme digestion sites are loaded at two terminals thereof respectively, and the gene fragments are linked to a vector pUC57 (produced by Suzhou GENEWIZ Biotechnology Co., Ltd). The UGT gene fragments were enzyme digested by using the restrictive endonucleases NdeI and BamHI, and purified fragments were recovered. The fragments were linked to the corresponding enzyme digestion site of the vector pTE30a by using a T4 ligase, and thus the fragments were transformed to the BL21 (DE3) strains.

The UGT strains were inoculated at a proportion of 1% into a 4 ml liquid LB medium, and the medium was shaken (at a speed of 200 rpm) at 37° C. overnight; the overnight culture was transferred at an inoculation amount of 1% into a 50 ml liquid LB medium, and was inoculated by shaking (at a speed of 200 rpm) at 37° C. until the OD600 value reached the range of 0.6 to 0.8; and then the IPTG having a concentration of 0.4 mM was added and overnight inoculation was carried out by shaking at 20° C. Upon completion of inducement, cells were centrifuged (8000 rpm and 10 min) and collected, the cells were resuspended by using a 5 ml 2 mmol/L phosphate buffer (having a pH value of 7.0) to obtain the recombinant cells containing the UGT-A.

Example 2: Preparation of UGT-A Lyophilized Powder

The recombinant cells containing the UGT-A prepared in Example 1 were further treated in ice bath and were ultrasonically crushed. A crushing liquid was centrifuged (8000 rpm and 10 min). Afterwards, a supernatant was collected and lyophilized for 24 h to obtain the lyophilized powder of the UGT-A.

Example 3: Preparation of Recombinant *Escherichia coli* Cells Containing the UGT-B In accordance with sequence 3 and sequence 4, the UGT-B gene fragments were genetically synthesized, NdeI and BamHI enzyme digestion sites were loaded at two terminals thereof respectively, and the gene fragments were linked to a vector pUC57 (produced by Suzhou GENEWIZ Biotechnology Co., Ltd). The UGT gene fragments were enzyme digested by using the restrictive endonucleases NdeI and BamHI, and purified fragments were recovered. The fragments were linked to the corresponding enzyme digestion site of the vector pTE30a by using a T4 ligase, and thus the fragments were transformed to the BL21 (DE3) strains.

The UGT strains were inoculated at a proportion of 1% into a 4 ml liquid LB medium, and the medium was shaken (at a speed of 200 rpm) at 37° C. overnight; the overnight culture was transferred at an inoculation amount of 1% into a 50 ml liquid LB medium, and was inoculated by shaking (at a speed of 200 rpm) at 37° C. until the OD600 value reached the range of 0.6 to 0.8; and then the IPTG having a concentration of 0.4 mM was added and overnight inoculation was carried out by shaking at 20° C. Upon completion of inducement, cells were centrifuged (8000 rpm and 10 min) and collected, the cells were resuspended by using a 5 ml 2 mmol/L phosphate buffer (having a pH value of 7.0) to obtain the recombinant cells containing the UGT-B for catalysis.

Example 4: Preparation of UGT-B Lyophilized Powder

The recombinant cells containing the UGT-B prepared in Example 3 were further treated in ice bath and were ultrasonically crushed. A crushing liquid was centrifuged (8000 rpm and 10 min). Afterwards, a supernatant was collected and lyophilized for 24 h to obtain the lyophilized powder of the UGT-B.

Example 5: Synthesis of Rebaudioside N by Using Rebaudioside J as a Reaction Substrate Under Catalysis of UDP-Glycosyltransferase (Route One)

In this example, the rebaudioside N was catalytically synthesized by using the UGT-A lyophilized powder prepared by the method in Example 2. In this example, a UDP-glucose regeneration system consisting of sucrose, sucrose synthase from *Arabidopsis thaliana* (hereinafter referred to as AtSUS1) and UDP was used as a glucose-based donor.

1 L of 0.05 mol/L phosphate buffer (having a pH value of 8.0), 0.5 g of UDP, 1 g of rebaudioside J, 5 g of sucrose, 10 g of UGT-A lyophilized powder, and 0.5 g of AtSUS1 lyophilized powder were added sequentially into the reaction system and uniformly mixed, and the resulted solution was then placed in water bath at 40° C., stirred at a speed of 300 rpm, and reacted for 24 h. Upon completion of the reaction, 500 μl of the reaction solution was taken and added into an equivalent volume of non-aqueous methanol for uniform mixture, and the resulted solution was centrifuged at a speed of 8000 rpm for 10 min. Afterwards, a supernatant was filtered by a filter membrane and tested by a high performance liquid chromatography (chromatographic conditions: chromatography column: Agilent eclipse SB-C18 4.6×150 mm; test wavelength: 210 nm; mobile phase: 0.1% solution of formic acid:acetonitrile=65%:35%; flow rate: 1.0 ml/min; and column temperature: 30° C.). A conversion rate of the rebaudioside J was over 90%. 0.61 g of the rebaudioside N was obtained through purification by silica gel-resin separation, crystallization and the like post-treatments, and the obtained rebaudioside N had a purity greater than 95%.

Example 6: Synthesis of Rebaudioside N by Using Rebaudioside a as a Reaction Substrate Under Catalysis of UDP-Glycosyltransferase (Route Two)

In this example, the rebaudioside N was catalytically synthesized by using the UGT-A lyophilized powder prepared by the method in Example 2 and the UGT-B lyophilized powder prepared by the method in Example 4.

Reaction in the first step: 1 L of 0.05 mol/L phosphate buffer (having a pH value of 8.0), 2 g of UDP rhamnosyl, 1 g of rebaudioside A, and 10 g of UGT-B lyophilized powder were sequentially added into the reaction system and uniformly mixed, and then the resulted solution was placed in water bath at 40° C., stirred at a speed of 300 rpm, and reacted for 24 h. Reaction in the second step: Upon completion of the reaction in the first step, the reaction solution was boiled for 10 min, the pH value of the reaction solution was regulated to 8.0, 0.5 g of UDP, 5 g of sucrose, 10 g of UGT-A lyophilized powder and 3 g of AtSUSI lyophilized powder were added and uniformly mixed, and the resulted solution was then placed in water bath at 40° C., stirred at a speed of 300 rpm, and reacted from 24 h. Upon completion of the reaction, 500 μl of the reaction solution was taken and added into an equivalent volume of non-aqueous methanol for uniform mixture, and the resulted solution was centrifuged at a speed of 8000 rpm for 10 min. Afterwards, a supernatant was filtered by a filter membrane and tested by a high performance liquid chromatography (chromatographic conditions: chromatography column: Agilent eclipse SB-C18 4.6×150 mm; test wavelength: 210 nm; mobile phase: 0.1% solution of formic acid:acetonitrile=65%:35%; flow rate: 1.0 ml/min; and column temperature: 30° C.). A conversion rate of the rebaudioside A was over 90%. 0.58 g of the rebaudioside N was obtained through purification by silica gel-resin separation, crystallization and the like post-treatments, and the obtained rebaudioside N had a purity greater than 95%.

Example 7: Synthesis of Rebaudioside N by Using Rebaudioside J as a Reaction Substrate Under Catalysis of the Recombinant Cells Containing the UDP-Glycosyltransferase In this example, the rebaudioside N was catalytically synthesized by using the recombinant cells containing the UGT-A prepared by the method in Example 1.

1 L of 0.05 mol/L phosphate buffer (having a pH value of 8.0), 0.5 g of UDP, 1 g of rebaudioside J, 5 g of sucrose, 40 g of UGT-A whole cells, and 10 g of AtSUS1 whole cells were added sequentially into the reaction system and uniformly mixed, and the resulted solution was then placed in water bath at 40° C., stirred at a speed of 300 rpm, and reacted for 24 h. Upon completion of the reaction, 500 μl of the reaction solution was taken and added into an equivalent volume of non-aqueous methanol for uniform mixture, and the resulted solution was centrifuged at a speed of 8000 rpm for 10 min. Afterwards, a supernatant was filtered by a filter membrane and tested by a high performance liquid chromatography (chromatographic conditions: chromatography column: Agilent eclipse SB-C18 4.6×150 mm; test wavelength: 210 nm; mobile phase: 0.1% solution of formic acid:acetonitrile=65%:35%; flow rate: 1.0 ml/min; and column temperature: 30° C.). A conversion rate of the rebaudioside J was over 90%. 0.54 g of the rebaudioside N was obtained through purification by silica gel-resin separation, crystallization and the like post-treatments, and the obtained rebaudioside N had a purity greater than 95%.

Example 8: Synthesis of Rebaudioside N by Using Rebaudioside a as a Reaction Substrate Under Catalysis of the Recombinant Cells Containing the UDP-Glycosyltransferase Reaction in the first step: 1 L of 0.05 mol/L phosphate buffer (having a pH value of 8.0), 2 g of UDP rhamnosyl, 1 g of rebaudioside A, and 40 g of UGT-B whole cells were sequentially added into the reaction system and uniformly mixed, then placed in water bath at 40° C., stirred at a speed of 300 rpm, and reacted for 24 h. Reaction in the second step: Upon completion of the reaction in the first step, the reaction solution was boiled for 10 min, the pH value of the reaction solution was regulated to 8.0, 0.5 g of UDP, 5 g of sucrose, 40 g of UGT-A whole cells, and 10 g of AtSUSI whole cells were added and uniformly mixed, and the resulted solution was then placed in water bath at 40° C., stirred at a speed of 300 rpm, and reacted from 24 h. Upon completion of the reaction, 500 μl of the reaction solution was taken and added into an equivalent volume of non-aqueous methanol for uniform mixture, and the resulted solution was centrifuged at a speed of 8000 rpm for 10 min. Afterwards, a supernatant was filtered by a filter membrane and tested by a high performance liquid chromatography (chromatographic conditions: chromatography column: Agilent eclipse SB-C18 4.6×150 mm; test wavelength: 210 nm; mobile phase: 0.1% solution of formic acid:acetonitrile=65%:35%; flow rate: 1.0 ml/min; and column temperature: 30° C.). A conversion rate of the rebaudioside A was over 90%. 0.53 g of the rebaudioside N was obtained through purification by silica gel-resin separation, crystallization and the like post-treatments, and the obtained rebaudioside N had a purity greater than 95%.

The above examples are merely intended to describe the technical concept and characteristics of the present invention, such that a person skilled in the art would better understand the disclosure of the present invention and practice the present invention. However, these examples shall not be construed to limit the protection scope of the present invention. Various equivalent variations or polishments made without departing from the spirit and essence of the present invention shall all be considered as falling within the protection scope of the present invention.

The invention claimed is:

1. An enzymatic method for preparing rebaudioside N, the method comprising reacting rebaudioside J with a glycosyl donor in a reaction system comprising: recombinant cells comprising a UDP-glycosyltransferase and/or a UDP-glycosyltransferase prepared therefrom, wherein the UDP-glycosyltransferase has the amino acid sequence according to SEQ ID NO: 2.

2. The method of claim 1, wherein the glycosyl donor is UDP-glucose or a UDP-glucose regeneration system comprising sucrose, sucrose synthase and UDP.

3. The method of claim 1, wherein the UDP-glycosyltransferase is UGT-A from *Stevia rebaudiana*.

4. The method of claim 1, wherein the reaction is carried out in an aqueous system at a temperature of 35 to 45° C. and at a pH of 7.5 to 8.5.

5. The method of claim 4, wherein the aqueous system comprises a phosphate buffer solution.

6. The method of claim 4, wherein the aqueous system further comprises a cell permeabilizing agent.

7. The method of claim 6, wherein the cell permeabilizing agent is toluene and wherein the toluene is present in the aqueous system at a concentration by volume of 1-3%.

8. The method of claim 1, wherein the recombinant cell is a cell of a microorganism.

9. The method of claim 8, wherein the microorganism is *Escherichia coli, Saccharomyces cerevisiae*, or *Pichia pastoris*.

10. The method of claim 1, further comprising purifying the rebaudioside N via resin isolation.

11. The method of claim 10, wherein the rebaudioside N purified via resin isolation has a purity greater than 95%.

* * * * *